(12) United States Patent
Ryufuku et al.

(10) Patent No.: US 6,852,499 B2
(45) Date of Patent: Feb. 8, 2005

(54) LUCIFERASE DETECTION REAGENT KITS AND LUCIFERASE DETECTION METHOD USING THE KIT

(75) Inventors: Masayuki Ryufuku, Tokyo (JP); Hozumi Tanaka, Fuchu (JP); Chie Suzuki, Tokyo (JP)

(73) Assignees: Toyo Ink Mfg. Co., Ltd.; Toyo B-Net Co., Ltd., Tokyo (JP)

( * ) Notice: Subject to any disclaimer, the term of this patent is extended or adjusted under 35 U.S.C. 154(b) by 0 days.

(21) Appl. No.: 10/386,567

(22) Filed: Mar. 13, 2003

(65) Prior Publication Data

US 2004/0043439 A1 Mar. 4, 2004

(30) Foreign Application Priority Data

Sep. 3, 2002 (JP) ........................................ 2002-257330

(51) Int. Cl.[7] .............................. C12Q 1/66; C12Q 1/02; C12N 9/02
(52) U.S. Cl. ............................... 435/8; 435/29; 435/189
(58) Field of Search ........................... 435/8, 189, 188, 435/975

(56) References Cited

U.S. PATENT DOCUMENTS

| 5,650,289 A | 7/1997 | Wood | 435/8 |
| 5,866,348 A | * 2/1999 | Scheirer | 435/8 |
| 6,171,809 B1 | 1/2001 | Roelant | 435/8 |

FOREIGN PATENT DOCUMENTS

| EP | 0 610 937 | 8/1994 |
| WO | WO 93/14222 | 7/1993 |

OTHER PUBLICATIONS

Webster's II New Riverside Dictionary (1984) (Houghton:Mifflin: Boston), p. 667.*

M. Ryufuku, et al., ITE Letters on Batteries, New Technologies & Medicine, vol. 3, No. 6, XP–009019430, pp. 713–719, "Low Amount of Diethyldithiocarbamate Enhances the Light Activity in Beetle Bioluminescence System in Vitro", 2002.

S. R. Ford, et al., Biochimica et Biophysica Acta, vol. 1252, No. 2, XP–009019380, pp. 180–184, "Does the Sulfhydryl or the Adenine Moiety of CoA Enhance Firefly Luciferase Activity?", 1995.

* cited by examiner

*Primary Examiner*—Jean C. Witz
*Assistant Examiner*—Susan Hanley
(74) *Attorney, Agent, or Firm*—Oblon, Spivak, McClelland, Maier & Neustadt, P.C.

(57) ABSTRACT

The present invention provides a detection method and a method of manufacturing a detection kit, both characterized by use of an organic sulfur reagent, and which are effective at low concentration of the reagent, are inexpensive, and have reduced unpleasant odor. Provided is a reagent kit for detecting a *Coleoptera luciferase*, comprising an organic sulfur reagent having the atomic sequence of sulfur-carbon-sulfur in its chemical structure, a luciferin, adenosine triphosphate and a magnesium ion. Also provide is a method for detecting a *Coleoptera luciferase*, comprising step 1 of mixing an aqueous solution, containing an organic sulfur reagent having the atomic sequence of sulfur-carbon-sulfur in its chemical structure, a luciferin, adenosine triphosphate and a magnesium ion, with a sample containing a *Coleoptera luciferase*, to give a mixed solution; and step 2 of measuring the light emitted in the mixed solution.

15 Claims, No Drawings

LUCIFERASE DETECTION REAGENT KITS AND LUCIFERASE DETECTION METHOD USING THE KIT

BACKGROUND OF THE INVENTION

The present invention relates to a reagent kit for detecting luminescence (light emission) from luciferin/luciferase reactions which is characterized by the use of an organic sulfur regent, and to a method for detecting a *Coleoptera luciferase* using the kit.

The detection kit provided according to the present invention is applicable to any assay system in which a *Coleoptera luciferase* enzyme is used as a reporter or signal.

In in vitro luciferin/luciferase luminescent reactions, a flash of light is observed as an emission pattern. Therefore, it has been impossible to determine such luminescent reactions precisely unless a specialized device that allows the injection of a measured amount of a luminescent reagent. To overcome this problem, a method for luciferase detection has been invented which uses a thiol reagent so that the half-life of the luminescence can be extended to about five minutes with increased quantity of light emission(Japanese Patent No. 3,171,595). According to this method, the quantity of light emitted from a luciferin/luciferase reaction can be determined precisely with a luminometer or liquid cintillation counter even if they do not have an automated luminescent reagent injection device. Since this method was invented, it has become possible to achieve sensitive determination of a luciferase expressed in cultured cells or the like by using a luciferase gene as a reporter gene. Thus, luciferin/luciferase luminescent reactions have been widely utilized.

However, the thiol reagents have unpleasant odor originated from a mercaptan residue, and the efficiency of measurement operation is poor. Dithiothreitol (DTT), which is described as a thiol regent in the patent publication above, is a very expensive reagent and, moreover, should be used in a high concentration of 5 mM or higher for achieving sufficient luciferin/luciferase reactions that measurement can be performed without any trouble. It is also known that DTT tends to be degraded readily in such a high concentration solution as described in the above patent publication and the DTT oxidized or degraded by dissolved oxygen or the like significantly reduces the efficiency of luciferin/luciferase reactions.

SUMMARY OF THE INVENTION

Accordingly, the object of the present invention is to provide a detection method and a kit which are inexpensive, have reduced mercaptan odor and can produce sufficient quantity of luminescence at low concentration.

The present invention relates to a reagent kit for detecting a *Coleoptera luciferase*, comprising an organic sulfur reagent having the atomic sequence of sulfur-carbon-sulfur in its chemical structure, a luciferin, adenosine triphosphate and a magnesium ion.

Using the reagent kit of the present invention, transcriptional activity of a gene can be determined. An example of the determination is briefly described below. A luciferase gene is incorporated into an expression vector along with a gene of interest. The vector is introduced in host cells. The luciferase gene is expressed in the transformed host cells along with the gene of interest. The quantity of light emitted from the luciferase is then measured using the reagent kit of the present invention. Based on the measurements, the amount of the luciferase expressed in the transformed host cells is determined. The transcriptional activity of the gene of interest can be determined based on the amount of the luciferase.

The present invention also relates to the kit for detecting a *Coleoptera luciferase*, which further comprises coenzyme A.

The present invention further relates to a method for detecting a *Coleoptera luciferase*, comprising:

step 1 of mixing an aqueous solution containing an organic sulfur reagent having the atomic sequence of sulfur-carbon-sulfur in its chemical structure, a luciferin, adenosine triphosphate and a magnesium ion with a sample containing a *Coleoptera luciferase* to give a mixed solution; and step 2 of measuring the light emitted in the mixed solution.

The present invention further relates to the method for detecting a *Coleoptera luciferase*, wherein the aqueous solution further contains coenzyme A.

The present invention still further relates to the method for detecting a *Coleoptera luciferase*, wherein the organic sulfur reagent is contained in the aqueous solution in a concentration of 0.01 mM to 200 mM, based on the total amount of the aqueous solution.

According to the present invention, a detection method and a kit which are inexpensive, have reduced mercaptan odor and can produce sufficient quantity of luminescence at low reagent concentration can be provided.

DESCRIPTION OF THE PREFERRED EMBODIMENTS

The luciferase used in the present invention is an enzyme that acts on a luciferin from firefly (order *Coleoptera*, family *Lampyridae*), a polyheterocyclic organic acid D-(−) -2-(6'-hydroxy-2'-benzothiazolyl)-$\Delta$2-thiazoline-4-carboxylic acid (hereinafter, simply referred to as "luciferin" unless otherwise specified) as a luminescence substrate, and which catalyzes the oxidation of the luciferin to produce photons. The luciferase includes any enzyme that participates in luminescent reactions originated from an insect belonging to *Coleoptera*, such as those luciferases from the families *Lampyridae, Elateridae, Omethidae* and *Rhagophthalmidae*. Also included are variants of these luciferases produced by recombinant DNA techniques, mutagenesis techniques and the like so that the stability of the enzyme proteins per se or the luminescent properties thereof are artificially modified.

The luciferin used in the present invention is a *Coleoptera* luciferin as stated above, including both of those luciferases extracted and purified directly from an insect belonging to the order *Coleoptera* and those luciferases synthesized chemically.

The coenzyme A (CoA) which can be used in the present invention may be one extracted and purified from yeast, including a lithium salt and a sodium salt thereof.

The organic sulfur reagent used in the present invention may be an organic sulfur reagent which has the atomic sequence of sulfur-carbon-sulfur in its chemical structure, so that it is capable of forming salts with organic amines and inorganic ammonium. The organic sulfur reagents capable of forming complexes with organic amines and inorganic ammonium may also be used.

In the case where the organic sulfur reagent is water-soluble or water-dispersible, it may be used in a free form.

The organic sulfur reagent that has the atomic sequence of sulfur-carbon-sulfur in its chemical structure and which can be used in the present invention includes, for example, dithiocarbamates, xanthogenates, thiophosphates and thiazoles.

Dithiocarbamates include, for example, piperidine pentamethylenedithiocarbamate, pipecoline methylpentamethyldithiocarbamate, zinc dimethyldithiocarbamate, zinc diethyldithiocarbamate, zinc dibutyldithiocarbamate, zinc ethylphenyldithiocarbamate, sodium dimethyldithiocarbamate, sodium diethyldithiocarbamate, sodium dibutyldithiocarbamate, potassium dimethyldithiocarbamate, copper dimethyldithiocarbamate, iron dimethyldithiocarbamate, lead ethylphenyldithiocarbamate, selenium diethyldithiocarbamate and tellurium diethyldithiocarbamate. However, the dithiocarbamates are not limited to these compounds, and any salt of any metal listed in the periodic table may also be used depending on the intended purposes.

Xanthogenates include, for example, potassium xanthogenate, zinc butylxanthogenate and sodium isopropylxanthogenate, but are not limited thereto and any xanthogenate capable of forming salts with any metal listed in the periodic table may also be used.

Thiophosphates include, for example, piperidine-bis(o,o-distearyldithiophosphate).

Thiazoles include, for example, 2-mercaptobenzothiazole, zinc 2-mercaptobenzothiazole, sodium 2-mercaptobenzothiazole, 2-mercaptobenzothiazole cyclohexylamine salt and copper 2-mercaptobenzothiazole. However, thiazoles are not limited to these compounds, and any one that is capable of forming a salt or complex with any metal listed in the periodic table may also be used. The organic sulfur reagents described above may be used singly or in combination.

The organic sulfur reagent is used in a concentration of 0.01 mM to 200 mM, preferably 0.1 mM to 5 mM.

In the detection kit and detection method according to the present invention, various surfactants and other additives may be added.

Table 1 summarizes examples of formulations of the detection kit according to the present invention.

TABLE 1

| | Most preferred conc. | | Preferred conc. range | | |
|---|---|---|---|---|---|
| | Conc. (mM) | Ratio to Ln | Minimum conc. | Maximum conc. | Suitable range |
| Luciferin (Ln) | 0.47 | 1.00 | 0.1 | 1 | 0.01 mM–10 mM |
| Organic sulfur compound | 3 | 6.38 | 0.1 | 5 | 0.01 mM–200 mM |
| Adenosine triphosphate | 0.53 | 1.13 | 0.03 | 1 | 0.01 mM–10 mM |
| Magnesium ion | 3.74 | 7.96 | 1 | 5 | 0.1 mM–10 mM |
| Coenzyme A | 0.27 | 0.57 | 0.1 | 1 | 0.01 mM–100 mM |
| Tricine (buffering component) | 20 | 42.55 | 10 | 50 | 5 mM–100 mM |

*All of the solvents are water (Milli-Q water; ultrapure water).

EXAMPLES

Hereinbelow, the present invention will be described in more detail with reference to the following examples, but the invention is not to be limited to these examples.

The luciferase used was one included in a commercially available kit (Toyo Ink Manufacturing Co., Ltd.; product No. PGL100).

Example 1

A "luciferase luminescent reagent" containing 20 mM tricine, 1.07 mM $(MgCO_3)_4Mg(OH)_2.5H_2O$, 2.67 mM magnesium sulfate, 0.1 mM EDTA, 270 $\mu$M CoA, 470 $\mu$M luciferin and 530 $\mu$M adenosine triphosphate (ATP), pH 7.8 was prepared in accordance with the formulation described in the instructions included in "PicaGene Luminescent Kit" (Toyo Ink Manufacturing Co., Ltd.; product No. PGL100), except that 33.3 mM dithiothreitol (DTT) mentioned in the instructions was not added. To the "luciferase luminescent reagent" was added sodium diethyldithiocarbamate at final concentrations of 0 mM, 0.33 mM, 3.3 mM and 33.3 mM.

An enzyme solution containing 100 ng/mL of luciferase was collected in 10 $\mu$L in a measurement cuvette of a luminometer (Berthold, LB9506). To the enzyme solution was added 100 $\mu$L of each of the "luciferase luminescent reagents" prepared above. Immediately after the addition, the resulting mixed solution was loaded on the luminometer, and the quantity of light emitted was measured for the initial 200 seconds of the reagent addition to determine the maximum quantity of light emitted (RLU/sec) during the period of measurement and the integrated quantity of light emitted for 200 seconds (RLU/200 sec) (Table 2).

In the luminescent system according to the present invention using an organic sulfur reagent without any thiol reagent (e.g., DTT), when a "luciferase luminescent reagent" containing sodium diethyldithiocarbamate was used, there was observed the occurrence of glow luminescence in which luminescence was attenuated gradually while maintaining a nearly constant value of light emission for 200 seconds, rather than flash luminescence in which luminescence is attenuated rapidly just after the addition of a reagent.

In the systems containing 0.33 mM and 3.3 mM of sodium diethyldithiocarbamate, the maximum quantity of light emitted (RLU/sec) was increased only slightly but there was observed an about 1.7-fold increase in the integrated quantity of light emitted (RLU/200 sec), which is a measure of the durability (lifetime) and stability of luminescence, as compared with the system containing no sodium diethyldithiocarbamate (0 mM). In the system containing sodium diethyldithiocarbamate at a concentration of as high as 33.3 mM, both of the maximum quantity of light emitted (RLU/sec) and the integrated quantity of light emitted (RLU/200 sec) tended to decrease to about two-fifths of those in the systems containing sodium diethyldithiocarbamate at lower concentrations (0.33 mM, 3.3 mM).

Example 2

A "luciferase luminescent reagent" containing 20 mM tricine, 1.07 mM $(MgCO_3)_4Mg(OH)_2.5H_2O$, 2.67 mM magnesium sulfate, 0.1 mM EDTA, 270 $\mu$M CoA, 470 $\mu$M luciferin and 530 $\mu$M adenosine triphosphate (ATP), pH 7.8 was prepared in accordance with the formulation described in the instructions included in "PicaGene Luminescent Kit" (Toyo Ink Manufacturing Co., Ltd.; product No. PGL100), except that 33.3 mM dithiothreitol (DTT) mentioned in the instructions was not added. To the "luciferase luminescent reagent" was added sodium dimethyldithiocarbamate at final concentrations of 0 mM, 0.33 mM 3.3 mM and 33.3 mM.

An enzyme solution containing 100 ng/mL of luciferase was collected in 10 μL in a measurement cuvette of a luminometer (Berthold, LB9506). To the enzyme solution was added 100 μL of each of the "luciferase luminescent reagents" prepared above. Immediately after the addition, the resulting mixed solution was loaded on the luminometer, and the quantity of light emitted was measured for the initial 200 seconds of the reagent addition to determine the maximum quantity of light emitted (RLU/sec) during the period of measurement and the integrated quantity of light emitted for 200 seconds (RLU/200 sec) (Table 2).

In the luminescent system according to the present invention using an organic sulfur reagent without any thiol reagent (e.g., DTT), when a "luciferase luminescent reagent" containing sodium dimethyldithiocarbamate was used, there was observed the occurrence of glow luminescence in which luminescence was attenuated gradually while maintaining a nearly constant value of light emission for 200 seconds, rather than flash luminescence in which luminescence is attenuated rapidly just after the addition of a reagent.

In the systems containing 0.33 mM and 3.3 mM of sodium dimethyldithiocarbamate, the maximum quantity of light emitted (RLU/sec) was increased only slightly but there was observed an about 1.7-fold increase in the integrated quantity of light emitted (RLU/200 sec), which is a measure of the durability and stability of luminescence, as compared with the system containing no sodium dimethyldithiocarbamate (0 mM). In the system containing sodium dimethyldithiocarbamate at a concentration of as high as 33.3 mM, both of the maximum quantity of light emitted (RLU/sec) and the integrated quantity of light emitted (RLU/200 sec) tended to decrease to about one-sixth of those in the systems containing sodium dimethyldithiocarbamate at lower concentrations (0.33 mM, 3.3 mM).

Example 3

A "luciferase luminescent reagent" containing 20 mM tricine, 1.07 mM $(MgCO_3)_4Mg(OH)_2.5H_2O$, 2.67 mM magnesium sulfate, 0.1 mM EDTA, 270 μM CoA, 470 μM luciferin and 530 μM adenosine triphosphate (ATP), pH 7.8 was prepared in accordance with the formulation described in the instructions included in "PicaGene Luminescent Kit" (Toyo Ink Manufacturing Co., Ltd.; product No. PGL100), except that 33.3 mM dithiothreitol (DTT) mentioned in the instructions was not added. To the "luciferase luminescent reagent" was added potassium xanthogenate at final concentrations of 0 mM, 0.33 mM 3.3 mM and 33.3 mM.

An enzyme solution containing 100 ng/mL of a luciferase which had been prepared by diluting "Luciferase Enzyme Standard (10 mg/mL)" included in "PicaGene Luminescent Kit" (Toyo Ink Manufacturing Co., Ltd.; product No. PGL100) with "PicaGene Cell Lysis Reagent (Toyo Ink Manufacturing Co., Ltd.; product No. PGC50) was collected in 10 μL in a measurement cuvette of a luminometer (Berthold, LB9506). To the enzyme solution was added 100 μL of each of the "luciferase luminescent reagents" prepared above. Immediately after the addition, the resulting mixed solution was loaded on the luminometer, and the quantity of light emitted was measured for the initial 200 seconds of the reagent addition to determine the maximum quantity of light emitted (RLU/sec) during the period of measurement and the integrated quantity of light emitted for 200 seconds (RLU/200 sec) (Table 2).

In the luminescent system according to the present invention using an organic sulfur reagent without any thiol reagent (e.g., DTT), when a "luciferase luminescent reagent" containing potassium xanthogenate was used, there was observed the occurrence of glow luminescence in which luminescence was attenuated gradually while maintaining a nearly constant value of light emission for 200 seconds, rather than flash luminescence in which luminescence is attenuated rapidly just after the addition of a reagent.

In the system containing 0.33 mM of potassium xanthogenate, the maximum quantity of light emitted (RLU/sec) was increased only slightly but there was observed an about 1.7-fold increase in the integrated quantity of light emitted (RLU/200 sec), which is a measure of the durability and stability of luminescence, as compared with the system containing no potassium xanthogenate (0 mM). In the system containing no potassium xanthogenate at a concentration of as high as 33.3 mM, both of the maximum quantity of light emitted (RLU/sec) and the integrated quantity of light emitted (RLU/200 sec) tended to decrease to about one-thirteenth of that in the system containing potassium xanthogenate at a lower concentration (0.33 mM).

Example 4

A "luciferase luminescent reagent" containing 20 mM tricine, 1.07 mM $(MgCO_3)_4Mg(OH)_2.5H_2O$, 2.67 mM magnesium sulfate, 0.1 mM EDTA, 270 μM CoA, 470 μM luciferin and 530 μM adenosine triphosphate (ATP), pH 7.8 was prepared in accordance with the formulation described in the instructions included in "PicaGene Luminescent Kit" (Toyo Ink Manufacturing Co., Ltd.; product No. PGL100), except that 33.3 mM dithiothreitol (DTT) mentioned in the instructions was not added. To the "luciferase luminescent reagent" was added 2-mercaptobenzothiazole at final concentrations of 0 mM, 0.33 mM 3.3 mM and 33.3 mM.

An enzyme solution containing 100 ng/mL of a luciferase which had been prepared by diluting "Luciferase Enzyme Standard (10 mg/mL)" included in "PicaGene Luminescent Kit" (Toyo Ink Manufacturing Co., Ltd.; product No. PGL100) with "PicaGene Cell Lysis Reagent (Toyo Ink Manufacturing Co., Ltd.; product No. PGC50) was collected in 10 μL in a measurement cuvette of a luminometer (Berthold, LB9506). To the enzyme solution was added 100 μL of each of the "luciferase luminescent reagents" prepared above. Immediately after the addition, the resulting mixed solution was loaded on the luminometer, and the quantity of light emitted was measured for the initial 200 seconds of the reagent addition to determine the maximum quantity of light emitted (RLU/sec) during the period of measurement and the integrated quantity of light emitted for 200 seconds (RLU/200 sec) (Table 2).

In the luminescent system according to the present invention using an organic sulfur reagent without any thiol reagent (e.g., DTT), when a "luciferase luminescent reagent" containing 2-mercaptobenzothiazole was used, there was observed the occurrence of glow luminescence in which luminescence was attenuated gradually while maintaining a nearly constant value of light emission for 200 seconds, rather than flash luminescence in which luminescence is attenuated rapidly just after the addition of a reagent.

In the systems containing 0.33 mM and 3.3 mM of 2-mercaptobenzothiazole, the maximum quantity of light emitted (RLU/sec) was increased only slightly but there was observed an about 1.7-fold increase in the integrated quantity of light emitted (RLU/200 sec), which is a measure of the durability and stability of luminescence, as compared with the system containing no 2-mercaptobenzothiazole (0 mM). In the system containing 2-mercaptobenzothiazole at a concentration of as high as 33.3 mM, both of the maximum quantity of light emitted (RLU/sec) and the integrated quantity of light emitted (RLU/200 sec) tended to decrease to nearly two-thirds of that in the system containing 2-mercaptobenzothiazole at a lower concentration (3.3 mM).

Comparative Example 1

A "luciferase luminescent reagent" containing 20 mM tricine, 1.07 mM $(MgCO_3)_4Mg(OH)_2 \cdot 5H_2O$, 2.67 mM magnesium sulfate, 0.1 mM EDTA, 270 μM CoA, 470 μM luciferin and 530 μM adenosine triphosphate (ATP), pH 7.8 was prepared in accordance with the formulation described in the instructions included in "PicaGene Luminescent Kit" (Toyo Ink Manufacturing Co., Ltd.; product No. PGL100), except that 33.3 mM dithiothreitol (DTT) mentioned in the instructions was not added. To the "luciferase luminescent reagent" was added-dithiothreitol (DTT) at final concentrations of 0 mM, 0.33 mM 3.3 mM and 33.3 mM.

An enzyme solution containing 100 ng/mL of luciferase was collected in 10 μL in a measurement cuvette of a luminometer (Berthold, LB9506). To the enzyme solution was added 100 μL of each of the "luciferase luminescent reagents" prepared above. Immediately after the addition, the resulting mixed solution was loaded on the luminometer, and the quantity of light emitted was measured for the initial 200 seconds of the reagent addition to determine the maximum quantity of light emitted (RLU/sec) during the period of measurement and the integrated quantity of light emitted for 200 seconds (RLU/200 sec) (Table 2).

When this "luciferase luminescent reagent" was used, there was observed the occurrence of glow luminescence in which luminescence was attenuated gradually while maintaining a nearly constant value of light emission for 200 seconds, rather than flash luminescence in which luminescence is attenuated rapidly just after the addition of a reagent.

In both of the systems containing 0.33 mM and 3.3 mM of DDT, there was observed little difference in the maximum quantity of light emitted (RLU/sec) as compared with the system containing no DDT (0 mM). However, the integrated quantity of light emitted (RLU/for 200 sec), which is a measure of the durability and stability of luminescence, increased with increasing DTT concentration. The maximum quantity of light emitted was observed at a concentration of as high as 33.3 mM, which was 1.8 times the value for the system without DTT.

The comparison of the results are shown in Table 2. It is found that the systems according to the present invention can provide sufficient quantity of luminescence at much lower concentrations of reagents compared with the systems using the conventional thiol reagent.

TABLE 2

| Final concentration (mM) | 0 | 0.33 | 3.3 | 33.3 |
|---|---|---|---|---|
| DTT | | | | |
| max RLU | 3,196,820 | 3,359,620 | 3,221,070 | 3,434,180 |
| RLU/200 | 369,659,741 | 511,723,424 | 579,940,160 | 667,250,048 |
| Sodium dimethyldithio-carbamate | | | | |
| max RLU | 3,196,820 | 3,432,620 | 3,212,010 | 560,080 |
| RLU/200 | 369,659,744 | 616,747,200 | 632,237,952 | 110,252,632 |

TABLE 2-continued

| Final concentration (mM) | 0 | 0.33 | 3.3 | 33.3 |
|---|---|---|---|---|
| Sodium diethyldithio-carbamate | | | | |
| max RLU | 3,196,820 | 3,267,710 | 3,141,880 | 1,261,630 |
| RLU/200 | 369,659,744 | 592,116,224 | 611,260,800 | 246,535,408 |
| Potassium xanthogenate | | | | |
| max RLU | 3,196,820 | 3,232,620 | 473,070 | 24,210 |
| RLU/200 | 369,659,744 | 616,747,200 | 92,549,720 | 4,519,292 |
| 2-mercapto-benzothiazole | | | | |
| max RLU | 3,196,820 | 3,267,710 | 3,410,350 | 2,603,090 |
| RLU/200 | 369,659,744 | 492,116,224 | 622,578,816 | 421,084,568 |

The entire disclosure of Japanese Patent Application No. 2002-257330 filed on Sep. 3, 2002 including specification, claims, drawings and summary is incorporated herein by reference in its entirety.

All publications, patents and patent applications cited herein are incorporated herein by reference in their entirety.

What is claimed is:

1. A reagent kit for detecting a *Coleoptera luciferase*, comprising an organic sulfur reagent having the atomic sequence of sulfur-carbon-sulfur in its chemical structure, a luciferin, adenosine triphosphate and a magnesium ion, and
   wherein the organic sulfur reagent is selected from the group consisting of dithiocarbamates, xanthozenates, thiophosphates and thiazoles.

2. The reagent kit for detecting a *Coleoptera luciferase* according to claim 1, which further comprises coenzyme A.

3. A method for detecting a *Coleoptera luciferase*, comprising:
   step 1 of mixing an aqueous solution containing an organic sulfur reagent having the atomic sequence of sulfur-carbon-sulfur in its chemical structure, a luciferin, adenosine triphosphate and a magnesium ion with a sample containing a *Coleoptera luciferase* to give a mixed solution; and
   step 2 of measuring the light emitted by the mixed solution, and
   wherein the organic sulfur reagent is selected from the group consisting of dithiocarbamates, xanthogenates, thiophosphates and thiazoles.

4. The method for detecting a *Coleoptera luciferase* according to claim 3, wherein the aqueous solution further contains coenzyme A.

5. The met hod for detecting a *Coleoptera luciferase* according to claim 3, wherein the organic sulfur reagent is contained in the aqueous solution in a concentration of 0.01 mM to 200 mM, based on the total amount of the aqueous solution.

6. The method for detecting a *Coleoptera luciferase* according to claim 4, wherein the organic sulfur reagent is contained in the aqueous solution in a concentration of 0.01 mM to 200 mM, based on the total amount of the aqueous solution.

7. The reagent kit for detecting a *Coleoptera luciferase* according to claim 1, wherein the organic sulfur reagent is contained in an aqueous solution in a concentration of 0.01 mM to 200 mM, based on the total amount of the aqueous solution.

8. The reagent kit for detecting a *Coleoptera luciferase* according to claim 1, wherein the dithiocarbamates are selected from piperidine pentamethylenedithiocarbamate, pipecoline methylpentamethyldithioctabamate, zinc dimetyldithiocarbamate, zinc diethyldithiocarbamate, zinc dibutyldithiocarbamate, zinc ethylphenyldithiocarbamate, sodium dimethyldithiocarbamate, sodium diethyldithiocarbamate, sodium dibutyldithiocarbamate, potassium dimethyldithiocarbamate, copper dimethi dithiocarbamate, iron dimethyldithiocarbamaate, lead ethylphenyldithiocarbamate, selenium diethyldithiocarbamate, tellurium diethyldithiocarbanate, a dithiocarbamate salt of any metal listed in the periodic table, or combinations thereof.

9. The reagent kit for detecting a *Coleoptera luciferase* according to claim 1, wherein the xanthogenates are selected from potassium xanthogenate, zinc butylxanthogenate, sodium isopropylxanthogenate, a xanthogenate salt of any metal listed in the periodic table, or combinations thereof.

10. The reagent kit for detecting a *Coleoptera luciferase* according to claim 1, wherein the organic sulfur reagent is piperidine-bis-(o,o-distearyldithiophosphate).

11. The reagent kit for detecting a *Coleoptera luciferase* according to claim 1, wherein the thiazoles are selected from 2-mercaptobenzothiazole, zinc 2-mercaptobenzothiazole, sodium 2-mercaptobenzothiazole, copper 2-mercaptobenzothiazole, 2-mercaptobenzothiazole cyclohexylamine salt, a thiazole salt of any metal listed in the periodic table, or combinations thereof.

12. The method for detecting a *Coleoptera luciferase* according to claim 3, wherein the dithiocarbamates are selected from piperidine pentamethylenedithiocarbamate, pipecoline methylpentamethyldithiocarbamate, zinc dimetyldithiocarbarnate, zinc diethyldithiocarbamate, zinc dibutyldithiocarbamate, zinc ethylphenyldithiocarbamate, sodium dimethyldithiocarbamate, sodium diethyldithiocarbamate, sodium dibutyldithiocarbamate, potassium dimethyldithiocarbamate, copper dimethyldithiocarbamate, iron dimethyldithiocarbamate, lead ethylphenyldithiocarbamate, selenium diethyldithiocarbamate, tellurium diethyldithiocarbamate, a dithiocarbamate salt of any metal listed in the periodic table, or combinations thereof.

13. The method for detecting a *Coleoptera luciferase* according to claim 3, wherein the xanthogenates are selected from potassium xanthogenate, zinc butylxanthogenate, sodium isopropylxanthogenate, a xanthogenate salt of any metal listed in the periodic table, or combinations thereof.

14. The method for detecting a *Coleoptera luciferase* according to claim 3, wherein the organic sulfur regent is piperidine-bis-(o,o-distearyldithiophosphate).

15. The method for detecting a *Coleoptera luciferase* according to claim 3, wherein the thiazoles are selected from 2-mercaptobenzothiazole, zinc 2-mercaptobenzothiazole, sodium 2-mercaptobenzothiazole, copper 2-mercaptobenzothiazole, 2-mercaptobenzothiazole cyclohexylamine salt, a thiazole salt of any metal listed in the periodic table, or combinations thereof.

* * * * *